United States Patent [19]

Kyo et al.

[11] 4,338,478
[45] Jul. 6, 1982

[54] PROCESS FOR PRODUCING CONJUGATED DIENES

[75] Inventors: Sunao Kyo; Katsumi Omura, both of Hasaki; Ken-ichi Hino, Funabashi, all of Japan

[73] Assignee: Kuraray Co., Ltd., Okayama, Japan

[21] Appl. No.: 218,018

[22] Filed: Dec. 18, 1980

[51] Int. Cl.$^3$ .............................................. C07C 1/24
[52] U.S. Cl. ................................ 585/606; 585/610; 585/639
[58] Field of Search ................. 585/606, 610, 639

[56] References Cited

U.S. PATENT DOCUMENTS 1,179,408  4/1916  Delbruck et al. .................... 585/610
3,890,404  6/1975  Takagi et al. ........................ 585/609

FOREIGN PATENT DOCUMENTS 1358188  6/1974  United Kingdom .

OTHER PUBLICATIONS

Chemical Abstracts; vol. 63; 8176f (1965).

*Primary Examiner*—Winston A. Douglas
*Assistant Examiner*—Jacqueline V. Howard
*Attorney, Agent, or Firm*—Wenderoth, Lind & Ponack

[57] ABSTRACT

A process for producing a conjugated diene represented by the general formula

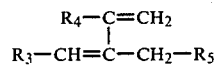

wherein $R_3$, $R_4$ and $R_5$ each represent a hydrogen atom, or any one of them represents a methyl group and the other two each represent a hydrogen atom, which comprises heating an alkane-1,3-diol represented by the general formula

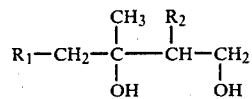

wherein $R_1$ and $R_2$ each represent a hydrogen atom, or one of them represents a hydrogen atom and the other represents a methyl group, to a temperature of at least 130° C. in the liquid phase in the presence of water and a boron-oxyacid or an oxygen-containing boron compound capable of forming a boron-oxyacid it under the reaction conditions.

7 Claims, No Drawings

PROCESS FOR PRODUCING CONJUGATED DIENES

This invention relates to a novel process for producing a conjugated diene from an alkane-1,3-diol by liquid-phase dehydration reaction. More specifically, it relates to a process for producing a conjugated diene represented by the general formula

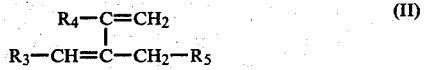

wherein $R_3$, $R_4$ and $R_5$ each represent a hydrogen atom, or any one of them represents a methyl group and the other two each represent a hydrogen atom, which comprises heating an alkane-1,3-diol represented by the general formula

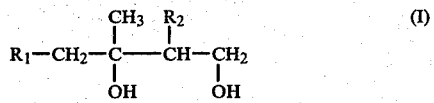

wherein both $R_1$ and $R_2$ each represent a hydrogen atom, or one of them represents a hydrogen atom and the other represents a methyl group,
to a temperature of at least 130° C. in the liquid phase in the presence of water and a boron-oxyacid or an oxygen-containing boron compound capable of forming a boron-oxyacid under the reaction conditions.

Dehydration reactions of alcohols intended for formation of double bonds have heretofore been performed in the vapor phase or the liquid phase. Generally, the vapor-phase reaction is carried out at a high temperature using a solid acid as a catalyst, and the liquid-phase reaction is carried out at a relatively low temperature using a strongly acidic substance as a catalyst. However, the reactions of forming double bonds by the dehydration of alcohols give quite different results depending upon the chemical structures (reactivities) of the starting alcohols and the resulting olefins.

The liquid-phase dehydration reaction of alcohols is advantageous over the vapor-phase dehydration reaction in that the reaction apparatus and operation are simple and the reaction temperature is relatively low. However, it tends to give rise to problems such as the corrosion of the apparatus and the reduction of the yield (increased consecutive side-reactions) because strong acids such as sulfuric acid, phosphoric acid, hydrohalic acids or sulfonic acid are used as the catalyst, and the starting alcohol and the resulting olefin reside in the reaction system for a relatively long period of time. For example, as in this invention, when the starting alkane-1,3-diol of general formula (I) has each of a primary and a tertiary hydroxyl group with different reactivity and the resulting diene of general formula (II) has high reactivity, it is difficult to obtain the diene in a good yield by the convention liquid phase reaction because of consecutive side-reactions giving by-products such as etheric, carbonylic, and polymeric compounds.

Chem. Abstracts, 63, 8176 f (1965) shows that when 3-methylbutane-1,3-diol is dehydrated in a 0.5-10% by weight aqueous solution of sulfuric acid, isoprene is obtained in a yield of only 66.5%.

British Pat. No. 1,358,188 discloses that isoprene is obtained in an improved yield by dehydrating 3-methylbutane-1,3-diol, 3-methyl-3-buten-1-ol or 2-methyl-3-buten-2-ol in the presence of an aqueous solution of an acid having a dissociation constant of at least $1 \times 10^{-6}$ and in the copresence of halogen ion.

U.S. Pat. No. 3,696,155 reports that when 3-methyl-3-buten-1-ol is reacted at a temperature of 20° to 250° C. in an aqueous solution of an acid having a dissociation constant of at least $1 \times 10^{-5}$ while distilling off the product in order to shorten the residence time of the product, the main product is 2-methyl-3-buten-2-ol and the formation of isoprene is in a small amount.

According to these prior methods, a special consideration must be given to the corrosion of the reaction apparatus.

It is an object of this invention to prevent the reduction of the yield of the main product caused by side-reactions and the corrosion of the reaction apparatus, which are frequently unfavorable to the production of the conjugated diene of general formula (II) from the alkane-1,3-diol of general formula (I).

In accordance with this invention, this object is achieved by heating the alkane-1,3-diol of general formula (I) to a temperature of at least 130° C. in the liquid phase of aqueous solution of a boron-oxyacid or an oxygen-containing boron compound capable of forming it under the reaction conditions.

The boron-oxyacid used as a catalytic component in the process of this invention is much weaker than inorganic acids heretofore used in the dehydration of alcohols. For example, ortho-boric acid has a dissociation constant of only $5 \times 10^{-10}$ (see, Lange's Handbook of Chemistry, page 1209, 1967, McGraw-Hill Book Co.). It is indeed surprising that in the present invention, the alkane-1,3-diol of general formula (I) can be dehydrated to the corresponding conjugated diene in a good yield by the catalytic action of an aqueous solution of such a weakly acidic boron-oxyacid. The alkane-1,3-diol of general formula (I) used as a starting material in the process of this invention specifically includes 3-methylbutane-1,3-diol, 3-methylpentane-1,3-diol and 2,3-dimethylbutane-1,3-diol, and among these, 3-methylbutane-1,3-diol is preferred. These diols do not have to be pure, and may contain impurities which do not cause any difficulty in separating the desired conjugated diene from the reaction mixture. For example, the diol may contain an alcohol resulting from liberation of one molecule of water from the diol. Examples of such alcohols are 3-methyl-3-buten-1-ol, 3-methyl-2-buten-1-ol, 2-methyl-3-buten-2-ol, 3-methyl-3-penten-1-ol, 3-methylenepentan-1-ol, 3-methyl-2-penten-1-ol, 3-methyl-1-penten-3-ol, 2,3-dimethyl-3-buten-1-ol, and 2,3-dimethyl-3-buten-2-ol. It is known that these alkenols are intermediates in the formation of the corresponding dienes from the above diols [Chem. Abstracts, 63, 8176 f ('65)], and by the process of this invention, these alkenols are dehydrated together with the diol to form dienes.

Furthermore, the diol of general formula (I) may form a mono- or di-ester with boric acid, because the boric acid ester of the diol rapidly changes to the diol and boric acid under the reaction conditions of the process of this invention.

The diols which may contain alkenols or the boric acid esters of the diols are known compounds, and can be easily produced industrially from tertiary olefins such as isobutene or isoamylene and formaldehyde either directly or through the corresponding 1,3-dioxane

[see Chem. Rev. 51, 505 (1951); and Japanese Laid-Open Patent Publication No. 109906/79].

Examples of the "aqueous solution of the boron-oxyacid" which performs a catalytic action in the process of this invention are aqueous solutions of ortho-boric acid, meta-boric acid, and tetra-boric acid.

Examples of the "oxygen-containing boron compound capable of forming a boron-oxyacid under the reaction conditions" are boric anhydride, borates of $C_1$–$C_6$ aliphatic alcohols such as methanol, ethanol, propanol, butanol, pentanol, 3-methyl-3-methoxybutanol, the alkenols mentioned hereinabove and the starting diols. These oxygen-containing boron compound may be used singly or in a combination of two or more. The "boron-oxyacid or the oxygen-containing boron compound capable of forming it under the reaction conditions" is used in combination with water in the process of this invention. Very desirably, the amount of this boron compound should be such that it can form an aqueous solution of boric acid in a concentration of at least 25% by weight as ortho-boric acid calculated on the assumption that the compound is wholly converted to ortho-boric acid under the reaction conditions. When the concentration of the aqueous solution of boric acid that may exist under the reaction conditions is less than 25% by weight, a practical rate of reaction cannot be obtained. The boron-oxyacid may exist in an amount, calculated as ortho-boric acid, which exceeds its solubility under the reaction conditions. In this case, the undissolved portion of the boron-oxyacid naturally disperses as fine crystals, but this does not specially hamper the practice of this invention. Even if, however, it is used in a larger amount than is necessary, no corresponding technical merit can be obtained.

The amount of water used together with the boron-oxyacid or the oxygen-containing boron compound capable of forming it under the reaction conditions is not critical, and can be varied widely depending upon the type of the boron-oxyacid or the oxygen-containing boron compound and the reaction conditions. When it is supposed that the boron compound is converted wholly to ortho-boric acid under the reaction conditions, it is advantageous that the weight ratio of the ortho-boric acid to water should be adjusted to at least 25:75, preferably from 30:70 to 60:40, more preferably from 40:60 to 50:50.

The reaction in accordance with this invention may be carried out at a temperature of at least 130° C. When the reaction temperature is lower than this limit, a practical rate of reaction cannot be obtained, and the yield of the desired diene tends to decrease greatly. The upper limit of the reaction temperature is not critical, but in view of the yield of the desired conjugated diene and the reaction pressure, a temperature of 230° C. is a suitable upper limit. In order to perform the reaction smoothly and to obtain a good yield, temperatures of 140° to 190° C. are preferred in practice. Generally, the reaction temperature is selected from the aforesaid range depending upon the concentration of boric acid in the aqueous medium under the reaction conditions. Usually, a lower temperature is preferred for a higher concentration of boric acid, and a higher temperature is preferred for a lower concentration.

Since the reaction must be performed in the liquid phase at the reaction temperature, it is usually performed under elevated pressure. A pressure at which the liquid phase boils under the reaction conditions is preferred. Generally, the reaction pressure may be the autogenous pressure of the reaction mixture boiling under the reaction conditions.

The process of this invention may be performed non-continuously (batchwise), but is advantageously carried out by a continuous operation. An especially preferred continuous operating method comprises continuously feeding the alkane-1,3-diol of general formula (I), and/or a borate of the alkane-1,3-diol (which may contain a free boron-oxyacid and/or a borate of an aliphatic monoalcohol having 1 to 6 carbon atoms) into an aqueous solution of the boron-oxyacid which is being stirred at a predetermined temperature and pressure, and simultaneously stripping the resulting conjugated diene from the reaction system together with water formed as a result of the reaction. In this method, it is possible to feed the starting alkane-1,3-diol and/or its borate in admixture with a certain fixed proportion of water while stripping the resulting conjugated diene together with the excess water in the reaction system. The boron-oxyacid present in the reaction system does not at all distill out, or distills out only slightly, during the reaction. Accordingly, when the free boron-oxyacid and/or the oxygen-containing boron compound capable of generating it under the reaction conditions is fed into the reaction system together with the starting alkane-1,3-diol, the excess of the boron-oxyacid can be continuously or non-continuously withdrawn and recovered from the reaction mixture as a slurry or an aqueous solution.

As is evident from the foregoing description, the aqueous solution of the boron-oxyacid or the oxygen-containing boron compound capable of generating it under the reaction conditions acts both as a catalyst and as a solvent for performing the reaction in the liquid phase.

Generally, when the concentration of the starting alkane-1,3-diol in the aqueous solution of the reaction system is lower, better results are obtained. It is suitably not more than 10% by weight, preferably not more than 5% by weight, based on the aqueous solution. Thus, when the reaction is carried out continuously, this concentration must be maintained by the rate of feeding the starting alkane-1,3-diol into the reaction system. Although the rate of feeding varies naturally depending upon the other reaction conditions, it is usually selected from a range of 120 to 480 g/hr per kilogram of the aqueous solution of the boron-oxyacid. If the concentration of the starting alkane-1,3-diol in the aqueous solution of the reaction system is too high, the amount of high-boiling by-products increases and these by-products are accumulated undesirably in the reaction system. As required, the aqueous solution of boron-oxyacid containing the high-boiling by-products and other materials may be taken out wholly or partly from the reaction system and purified by known methods such as extraction, concentration or re-crystallization for re-use.

As stated hereinabove, the conjugated diene formed in the reaction system is rapidly stripped from the reaction system by water, separated from the aqueous layer in an oil-water separator (decanter), and then purified in a distillation column. The separated aqueous layer may, as required, be partly recycled to the reactor.

In the process of this invention, a solvent or diluent (other than water) which is inert to the reaction may be used with water to strip the resulting conjugated diene rapidly from the reaction system. The solvent or diluent used for this purpose is a liquid volatile organic compound which boils under the reaction conditions. Examples are aliphatic, alicyclic and aromatic hydrocarbons such as benzine fractions, hexane, cyclohexane, methylcyclohexane, benzene, toluene and xylene.

Thus, according to the process of this invention, the conjugated diene of general formula (II) can be obtained in a high yield with a high selectivity. The process of this invention can be especially advantageously applied to the production of isoprene corresponding to general formula (II) in which $R_3$, $R_4$ and $R_5$ are all hydrogen atoms.

The conjugated dienes of general formula (II) obtained by the process of this invention are very important as raw materials for synthetic rubbers, terpene compounds and other useful compounds in the polymer industry and in chemical industry dealing with perfumes, medicines and agricultural chemicals.

The following Examples illustrate the present invention more specifically. It should be understood that the invention is in no way limited by these examples.

EXAMPLE 1

A 300 ml electromagnetically stirred pressure resistant glass reactor equipped with a material feed inlet, a thermometer and a condenser connected to a receiver was charged with 40 g of ortho-boric acid and 60 g of water, and with stirring, they were heated to form an aqueous solution of ortho-boric acid. Then, the aqueous solution was maintained at 180° C., and with stirring, a 20% by weight aqueous solution of 3-methylbutane-1,3-diol was introduced into it at a rate of 55.2 g/hr by means of a pressure-resistant micro-metering pump, and allowed to react. Simultaneously with the introduction of this starting material, isoprene formed. It was stripped from the reaction system together with water. After introducing the starting material over a total period of 5 hours, water alone was introduced at the same rate for 20 minutes and then the reaction was stopped. During the feeding of the starting material, the amount of the liquid in the reaction system was maintained almost constant. At this time, the pressure of the reaction system was 6.8 kg/cm².G.

The distillate was separated into an organic layer and an aqueous layer, and the organic layer was analyzed by gas-liquid chromatography. The aqueous layer was analyzed for ortho-boric acid by the flame reaction and titrated by the mannitol method, and no ortho-boric acid was detected. The organic compounds dissolved in the aqueous layer was extracted by continuous extraction with diethyl ether, and analyzed by gas-liquid chromatography.

The aqueous solution of ortho-boric acid remaining in the reactor was cooled to precipitate ortho-boric acid which was then separated by filtration and recovered. The filtrate was treated in the same way as in the case of the aqueous layer of the distillate, and analyzed for remaining organic compounds. The results of the reaction were as follows:

| | |
|---|---|
| Conversion of 3-methylbutane-1,3-diol: | 99.0% |
| Selectivity for | |
| Isoprene | 91.8% |
| 2-Methyl-3-buten-2-ol | 1.4% |
| 3-Methyl-3-buten-1-ol | 2.6% |
| 3-Methyl-2-buten-1-ol | 1.6% |
| 2-Methylbutan-1-al and | |
| 3-methylbutan-2-one | 0.9% |

EXAMPLES 2 TO 5

Example 1 was repeated except that the ratio of ortho-boric acid to water in the aqueous solution of the catalyst (ortho-boric acid), the reaction temperature and the rate of feeding an aqueous solution of the starting material were changed as shown in Table 1. The results are shown in Table 1.

TABLE 1

| Example | | 2 | 3 | 4 | 5 |
|---|---|---|---|---|---|
| Composition of the charged aqueous solution of boric acid (g of boric acid/g of water) | | 50/50 | 50/50 | 50/50 | 60/40 |
| Rate of feeding an aqueous solution of the starting material (g/hr) | | 62.0 | 62.0 | 62.0 | 66.0 |
| Reaction temperature (°C.) | | 160 | 170 | 180 | 150 |
| Reaction pressure (kg/cm² . G) | | 3.3 | 4.6 | 6.0 | 2.1 |
| Conversion (%) | | 98.6 | 99.2 | 99.8 | 95.5 |
| Selectivity (%) | Isoprene | 79.3 | 85.5 | 75.7 | 81.0 |
| | 2-Methyl-3-buten-2-ol | 1.7 | 1.1 | 1.3 | 1.7 |
| | 3-Methyl-3-buten-1-ol | 2.1 | 1.3 | 1.0 | 2.8 |
| | 3-Methyl-2-buten-1-ol | 1.4 | 1.2 | 0.3 | 1.2 |
| | 2-Methylbutan-1-al and 3-methylbutan-2-one | 2.8 | 3.2 | 6.1 | 1.1 |

In the foregoing Examples, the coloration of the aqueous solution of boric acid was slight, and the amounts of high-boiling products accumulated in the aqueous solution of boric acid were very small.

EXAMPLE 6

Using the same apparatus as in Example 1, a 40% by weight aqueous solution of 2,3-dimethylbutane-1,3-diol was reacted in the same way as in Example 1 while it was fed at a rate of 90 g/hr to a 45% by weight aqueous solution of orthoboric acid maintained at 170° C. The reaction product was worked up and analyzed in the same way as in Example 1. The results were as follows:

| | |
|---|---|
| Conversion of 2,3-dimethylbutane-1,3-diol | 98.6% |
| Selectivity for | |
| 2,3-Dimethylbutadiene | 90.7% |
| 2,3-Dimethyl-3-buten-2-ol | 2.1% |
| 3-Methyl-2-buten-1-ol | 0.8% |
| 3-Methyl-3-buten-1-ol | 3.0% |

EXAMPLE 7

The same reactor as used in Example 1 was charged with 114 g of water and 75 g of methyl orthoborate, and with stirring, they were heated until the temperature of the mixture reached 170° C. under a pressure of 5.7 kg/cm².G, while distilling off methanol generated. During this time, 69 g of methanol and 18 g of water were distilled off. Then, under these conditions, a 40% by weight aqueous solution of 3-methylbutane-1,3-diol was fed into the reaction system at a rate of 90 g/hr for 3 hours, and allowed to react in the same way as in Example 1. Simultaneously with the termination of the feeding of the starting material, the reaction was stopped. The reaction mixture which was obtained for the last one hour of the reaction period was analyzed in the same way as in Example 1. The results were as follows:

| | |
|---|---|
| Conversion of 3-methylbutane-1,3-diol | 98.2% |
| Selectivity for | |
| Isoprene | 89.5% |
| 2-Methyl-3-buten-2-ol | 1.87% |
| 3-Methyl-2-buten-1-ol | 0.25% |
| 3-Methyl-3-buten-1-ol | 3.20% |
| 2-Methylbutan-1-al and | |
| 3-methylbutan-2-one | 0.85% |

EXAMPLE 8

(1) A 5-liter electromagnetically stirred autoclave was charged with 465 g of ortho-boric acid, 360 g of a 50% by weight aqueous solution of formaldehyde, 370 g of tertiary butanol and 1064 g of isobutene, and with stirring, they were heated to 150° C. over the course of about 100 minutes. The mixture was allowed to react at this temperature for 1.5 hours, and immediately then, the autoclave was cooled. The pressure at the end of the reaction was 31 kg/cm².G. When the temperature of the reaction mixture dropped to 50° C. as a result of cooling, the cock was opened with stirring, and the unreacted isobutene and other low-boiling compounds were conducted to a dry ice/acetone trap where they were condensed and recovered. The autoclave was then opened, and the contents were filtered. Boric acid thus precipitated was recovered by filtration. A part of 1718 g of the aqueous solution consisting of the washing water used in the filtration and the filtrate was sampled, and analyzed for boric acid and formaldehyde. At the same time, the remaining boric acid was removed by an ion exchange resin (Amberlite IRA 400, Trademark), and the dissolved organic compounds were analyzed by gas-liquid chromatography. It was found that the entire reaction mixture had the following composition.

| | |
|---|---|
| Formaldehyde | 0 g |
| Tertiary butyl alcohol | 538.6g (31.35%) |
| 4-Methyl-5,6-dihydro-2H-pyran | 11.3g (0.65%) |
| 3-Methyl-3-buten-1-ol | 19.3g (1.12%) |
| 4,4-Dimethyl-1,3-dioxane | 40.8g (2.37%) |
| 3-Methylbutane-1,3-diol | 459.1g (26.72%) |
| Unidentified organic matter | 65.7g (3.82%) |
| Boric acid (as ortho-boric acid) | 184.0g (10.71%) |
| Water | 399.7g (23.26%) |

(2) A 500 ml electromagnetically stirred pressure-resistant glass reactor equipped with a material feed inlet, a thermometer and a condenser connected to a pressure-resistant receiver was charged with 174 g of ortho-boric acid and 126 g of water, and with stirring, they were heated to form an aqueous solution of ortho-boric acid. The aqueous solution was maintained at 150° C. Then, the reaction mixture having the above composition obtained by the procedure (1) was continuously fed into the aqueous solution at a rate of 253.6 g/hour for 3 hours by means of a pressure-resistant metering pump, and allowed to react. Simultaneously, the product was distilled off together with water. During the reaction, the pressure was maintained at 3.1 to 3.2 kg/cm².G. Heating was regulated so that the amount of the distilate was nearly balanced with that of the feed. Upon starting of the reaction, boric acid introduced together with the starting material was seen to precipitate into slurry in the reaction system. After the reaction, the distillate and the aqueous solution of boric acid in the reactor were worked up and analyzed in the same way as in Example 1. The results are shown below. The percentages of these products are mole% based on the amount of formaldehyde used initially.

| | |
|---|---|
| Isoprene | 83.6% |
| 3-Methyl-3-buten-1-ol | 0.3% |
| 2-Methylbutan-1-al and | |
| 3-methylbutan-2-one | 1.4% |
| 4-Methyl-5,6-dihydro-2H-pyran | 4.7% |

What we claim is:

1. A process for producing a conjugated diene represented by the general formula

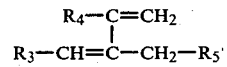

wherein $R_3$, $R_4$ and $R_5$ each represent a hydrogen atom, or any one of them represents a methyl group and the other two each represent a hydrogen atom, which comprises heating an alkane-1,3-diol represented by the general formula

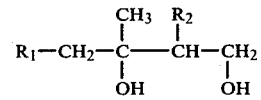

wherein $R_1$ and $R_2$ each represent a hydrogen atom, or one of them represents a hydrogen atom and the other represents a methyl group, to a temperature of at least 130° C. in the liquid phase in the presence of water and a boron-oxyacid or an oxygen-containing boron compound capable of forming a boron-oxyacid in situ in a weight ratio such that the boron-oxyacid or compounds producing such compound is in a weight ratio of at least 25:75 in respect to the water, calculated on the assumption that the boron-oxyacid compound or compounds producing such compound is converted wholly to ortho-boric acid.

2. The process of claim 1 wherein the alkane-1,3-diol is 3-methylbutane-1,3-diol.

3. The process of claim 1 wherein the conjugated diene is isoprene.

4. The process of claim 1 wherein the boron-oxyacid is ortho-boric acid, meta-boric acid or tetraboric acid, and the oxygen-containing boron compound is boric anhydride or a borate of an aliphatic alcohol having 1 to 6 carbon atoms.

5. The process of claim 1 wherein the concentration of the alkane-1,3-diol in the reaction system is at most 10% by weight.

6. The process of claim 1 wherein the heating is carried out at a temperature of 140° to 190° C.

7. The process of claim 1 wherein the reaction is carried out while distilling off the reaction product from the reaction system.

\* \* \* \* \*

UNITED STATES PATENT AND TRADEMARK OFFICE
CERTIFICATE OF CORRECTION

PATENT NO. : USP 4,338,478

DATED : July 6, 1982

INVENTOR(S) : KYO ET AL.

It is certified that error appears in the above-identified patent and that said Letters Patent is hereby corrected as shown below:

Cover Page, Col. 2, last line of the "Abstract," before "under" delete "it".

Column 1, line 62, change "convention" to -- conventional --.

Column 1, line 65, change "63" to -- $\underline{63}$ --.

Column 2, line 28, change "it" to -- boron oxyacid --.

Column 2, line 56, change "63" to -- $\underline{63}$ --.

Column 3, line 1, change "51" to -- $\underline{51}$ --.

UNITED STATES PATENT AND TRADEMARK OFFICE
CERTIFICATE OF CORRECTION

PATENT NO. : USP 4,338,478

DATED : July 6, 1982

INVENTOR(S) : KYO ET AL.

It is certified that error appears in the above-identified patent and that said Letters Patent is hereby corrected as shown below:

Column 4, line 28, delete "and recovered".

Signed and Sealed this

Twelfth Day of February 1985

[SEAL]

Attest:

DONALD J. QUIGG

Attesting Officer     Acting Commissioner of Patents and Trademarks